US00PP28834P3

(12) United States Plant Patent
Pierron-Darbonne

(10) Patent No.: US PP28,834 P3
(45) Date of Patent: Jan. 2, 2018

(54) STRAWBERRY PLANT NAMED 'PLANASA 0949'

(50) Latin Name: *Fragaria×ananassa*
Varietal Denomination: Planasa 0949

(71) Applicant: Plantas de Navarra, S.A., Navarra (ES)

(72) Inventor: Alexandre Pierron-Darbonne, Pamplona (ES)

(73) Assignee: PLANTAS DE NAVARRA, S.A., Navarra (ES)

( * ) Notice: Subject to any disclaimer, the term of this patent is extended or adjusted under 35 U.S.C. 154(b) by 43 days.

(21) Appl. No.: 14/999,502

(22) Filed: May 16, 2016

(65) Prior Publication Data

US 2017/0127587 P1 May 4, 2017

(30) Foreign Application Priority Data

Oct. 29, 2015 (QZ) ..... PBR 2015/2490

(51) Int. Cl.
*A01H 5/08* (2006.01)

(52) U.S. Cl.
USPC ..... Plt./208

(58) Field of Classification Search
USPC ..... Plt./208
See application file for complete search history.

(56) References Cited

PUBLICATIONS

UPOV hit on strawberry plant named 'Planasa 0949', QZ PBR 2015/2490, application date Oct. 29, 2015.*
UPOV hit on strawberry plant named 'Planasa 0949', QZ PBR 20150263, application date Oct. 22, 2015.*

* cited by examiner

*Primary Examiner* — Anne Grunberg
(74) *Attorney, Agent, or Firm* — Knobbe, Martens, Olson & Bear, LLP

(57) ABSTRACT

Described herein is a new and distinct strawberry variety with varietal denomination 'Planasa 0949', characterized by a combination of traits which include, but are not limited to, inflorescence that appears level with the foliage, larger size of calyx relative to corolla and abundant production of medium-sized red colored, conical shaped, and firm fruits, with orange red colored flesh, with early time of flowering and ripening. 'Planasa 0949' is a not remontant variety.

14 Drawing Sheets

Botanical classification: *Fragaria×ananassa.*
Variety denomination: The new plant has the varietal denomination 'Planasa 0949'.

CROSS-REFERENCE TO RELATED APPLICATIONS

This application claims the benefit of European Community Plant Variety Office Application No. 2015/2490, for a strawberry variety named 'Planasa 0949', filed on Oct. 29, 2015, the entirety of which is incorporated by reference herein.

BACKGROUND

Disclosed herein is a new and distinct strawberry variety. The varietal denomination of the new variety is 'Planasa 0949'. The new variety was designated by the breeder as '09.24.04'. The new variety of strawberry was created in a breeding program by crossing two parents in 2009 in Cartaya (Huelva), Spain about 7° W, 37° N, 45 feet elevation; in particular, by crossing as seed parent an undistributed strawberry parent designated '09-024' (unpatented) and as pollen parent an undistributed strawberry parent designated '03-98' (unpatented).

Both the seed and pollen parental cultivars were obtained by Plantas de Navara, S.A. Both parental cultivars are selections from breeder's program of Plantas de Navarra, S.A.

The resulting seedling of the new variety was grown and asexually propagated by Alexandre Pierron-Darbonne by runners in Segovia, Spain, 3° 59'W., 41° 22'N., 2742 feet elevation and it was successively propagated by runners first into a Screen-House, and after in the fields. Plants of the new variety were further asexually propagated and extensively tested. In order to establish and bring to health the initial head clones, mother plants that had developed several stolons were subjected to a heat treatment, or Thermotherapy, at 36° C.-37° C. for 3 to 4 weeks. After that treatment, apical meristems were cut and developed (1 apical meristem corresponding to 1 rooting plant) in a vitro culture for 5 to 6 weeks. This propagation and testing has demonstrated that the combination of traits disclosed herein which characterize the new variety are fixed and retained true to type through successive generations of asexual reproduction.

The growing period in Cartaya (Huelva), Spain, about 7° W, 37° N, 45 feet elevation, where the observations were made, is between about October 13 and May 11 of each year with a date of first flowering on November 11. The location where the observations were made is Cartaya (Huelva), Spain and it is believed to apply to plants grown under similar conditions of soil and climate elsewhere. 'Planasa 0949' is a short variety that benefits from induction to flowering by chilling, usually a few hours are sufficient, preferably at temperatures of 7° C. or less. Normally, the minimum number of hours is accumulated in the field during several days.

SUMMARY

Among the characteristics which appear to distinguish the new variety from other varieties are a combination of traits which include inflorescence that appears level with the foliage, larger size of calyx relative to corolla and abundant production of medium red colored, conical shaped, and firm fruit, medium fruit size, orange red colored flesh, early time of flowering and ripening. 'Planasa 0949' is a not remontant variety.

The new variety 'Planasa 0949' is distinguished from others cultivars by showing the inflorescence at same level with the foliage, the shape of the base of terminal leaflet is acute, it shows a conical shape fruit with a medium red color, the fruit is firm and it shows a medium size with an orange red colored flesh and it has early flowering and ripening times.

COMPARISON TO THE PARENTS

The new variety 'Planasa 0949' is distinguished therefrom its seed parent '09-024' (unpatented) in that the length in relation to width of terminal leaflet is equal in the seed parent, but is moderately longer in Planasa 0949. Additionally, the shape in cross section of terminal leaflet is straight in the seed parent, but is concave in Planasa 0949. Additionally, the stipule shows a medium anthocyanin coloration in the seed parent, but anthocyanin coloration is absent or very weak (RHS yellow-green group coloration, near 145 D to 145 C) in Planasa 0949. Additionally, the seed parent shows a dark red fruit (RHS red group color, near 44 B to 44 A) with a medium red color of flesh (RHS red group color, near 43 B to 43 A), while Plasana 0949 shows fruit in RHS red group (near 41 A to 42 A), with secondary fruit flesh that is orange red (RHS orange-red group near 33 B to 33 A), lightening toward center.

The new variety 'Planasa 0949' is distinguished there from its pollen parent '03-98' (unpatented) in that for the pollen parent, the leaf color of upper side is dark green (RHS green group color, near 135 A to 136 A) with medium glossiness, the length in relation to width of terminal leaflet is much longer, the pollen parent shows a large fruit size, with a medium red color of flesh (RHS red group color, near 43 B to 43 A).

COMPARISON TO CLOSEST VARIETY

The new variety 'Planasa 0949' is closest to the variety 'Sabrina' (U.S. Plant Pat. No. 22,506) but is distinguished by the following characteristics possessed by 'Planasa 0949' which are different than, or not possessed by, 'Sabrina' (U.S. Plant Pat. No. 22,506).

Terminal leaflet in 'Sabrina' (U.S. Plant Pat. No. 22,506) is much longer than broad, whereas in 'Planasa 0949' is moderately longer than broad.

Leaf of 'Sabrina' (U.S. Plant Pat. No. 22,506) shows a RHS green group color in the upperside (near 135 A to 136 A), whereas the new variety 'Planasa 0949' shows a RHS green group color in the upperside (near 138 A to 139 B).

Fruit size in 'Sabrina' (U.S. Plant Pat. No. 22,506) is larger than in 'Planasa 0949'.

'Sabrina' (U.S. Plant Pat. No. 22,506) shows a red fruit color (RHS red group near 43 B to 43 A), whereas in 'Planasa 0949' it is an medium red fruit color (RHS red group near 41 A to 42 A).

Color of flesh in fruits of 'Sabrina' (U.S. Plant Pat. No. 22,506) is red (RHS red group near 41 B to 41 A), whereas the color of flesh in fruits of 'Planasa 0949' is orange red (RHS orange-red group near 33 B to 33 A), lightening toward the center.

Time of beginning of flowering and fruit ripening of 'Planasa 0949' is earlier than 'Sabrina' (U.S. Plant Pat. No. 22,506).

Differences in length/width ratio in the terminal leaflet of 'Planasa 0949' (designated 09.24.04) and 'Sabrina' (U.S. Plant Pat. No. 22,506) are shown in FIG. 6. Differences in the upperside color of leaf of 'Planasa 0949' (designated 09.24.04) and 'Sabrina' (U.S. Plant Pat. No. 22,506) are shown in FIG. 5. Differences in fruit size and fruit color of 'Planasa 0949' (designated 09.24.04) and 'Sabrina' (U.S. Plant Pat. No. 22,506) are shown in FIG. 13. Differences in the fruit flesh color 'Planasa 0949' (designated 09.24.04) and 'Sabrina' (U.S. Plant Pat. No. 22,506) are shown in FIG. 14. These differences are maintained during the harvest season.

Plant growth habit is upright in 'Planasa 0949' whereas it semi-upright in 'Sabrina' (U.S. Plant Pat. No. 22,506).

Foliage density is medium in 'Planasa 0949' and dense in 'Sabrina' (U.S. Plant Pat. No. 22,506).

Plant vigor is medium in 'Planasa 0949' and strong in 'Sabrina' (U.S. Plant Pat. No. 22,506).

Stolon anthocyanin coloration is absent or very weak in 'Planasa 0949' and medium in 'Sabrina' (U.S. Plant Pat. No. 22,506).

The shape of base of terminal leaflet is acute in 'Planasa 0949'. In comparison, it is obtuse in 'Sabrina' (U.S. Plant Pat. No. 22,506).

Terminal leaflet margin is crenate in 'Planasa 0949' and serrate to crenate in 'Sabrina' (U.S. Plant Pat. No. 22,506).

Petiole length is medium in 'Planasa 0949' and long in 'Sabrina' (U.S. Plant Pat. No. 22,506).

The attitude/position of pedicel hairs is slightly outwards in 'Planasa 0949' and upwards in 'Sabrina' (U.S. Plant Pat. No. 22,506).

The arrangement of flower petals is overlapping in 'Planasa 0949', whereas it is touching in 'Sabrina' (U.S. Plant Pat. No. 22,506).

Petal length/width ratio is equal in 'Planasa 0949'. In comparison, it is moderately longer in 'Sabrina' (U.S. Plant Pat. No. 22,506).

The length/width ratio of fruit in 'Planasa 0949' is moderately longer whereas length/width ratio in 'Sabrina' (U.S. Plant Pat. No. 22,506) is much longer than broad.

The fruit size in 'Planasa 0949' is medium whereas in 'Sabrina' (U.S. Plant Pat. No. 22,506) it is large.

The difference if shape of primary and secondary fruits is slight in 'Planasa 0949'. In comparison, it is moderate in 'Sabrina' (U.S. Plant Pat. No. 22,506).

The fruit color in 'Planasa 0949' is medium red fruit color whereas 'Sabrina' (U.S. Plant Pat. No. 22,506) shows a dark red fruit color.

In the fruit, the width of the band without achenes is absent or very narrow in 'Planasa 0949' whereas it is narrow in 'Sabrina' (U.S. Plant Pat. No. 22,506).

Insertion/position of achenes in fruits of 'Planasa 0949' is below surface, whereas in 'Sabrina' (U.S. Plant Pat. No. 22,506) it is level with surface.

Attitude of sepals in the fruit is outwards in 'Planasa 0949' whereas it upwards in 'Sabrina' (U.S. Plant Pat. No. 22,506).

Diameter of calyx in relation to diameter of fruit is slightly larger in 'Planasa 0949' whereas it is the same size in 'Sabrina' (U.S. Plant Pat. No. 22,506).

Flowering and fruit ripening are early for 'Planasa 0949' whereas they are medium for 'Sabrina' (U.S. Plant Pat. No. 22,506).

BRIEF DESCRIPTION OF THE ILLUSTRATIONS

The accompanying photographs show typical specimens of the new variety, designated 09.24.04 in the illustrations, including fruit, foliage and flower, in color as nearly true as it is reasonably possible to make in color illustrations of this character.

The plants depicted in the drawings were planted October 13 in the farm of La Mogalla in Cartaya (Huelva), Spain, about 7° W, 37° N, 45 feet elevation.

Drawings/photographs were taken March-April (about March 25 and April 8): minimum temperate about 10 to 12° Centigrade, maximum temperate about 22 to 24° Centigrade.

FIG. 2 shows several plants of the new variety (designated 09.24.04) which exhibit an upright habit, a medium density plant and the position of the inflorescence relative to foliage is level with.

Figure 1:
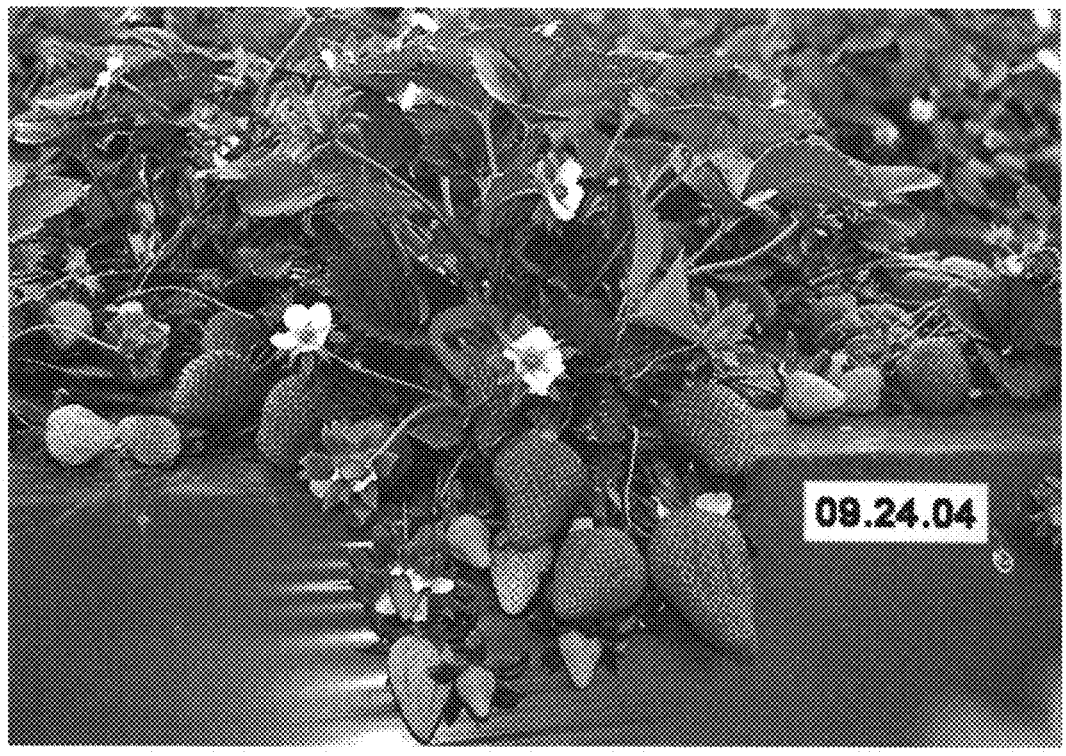
FIG. 1 shows several plants of the new variety (designated 09.24.04) with several medium red colored and conical shape fruits.
Figure 2:
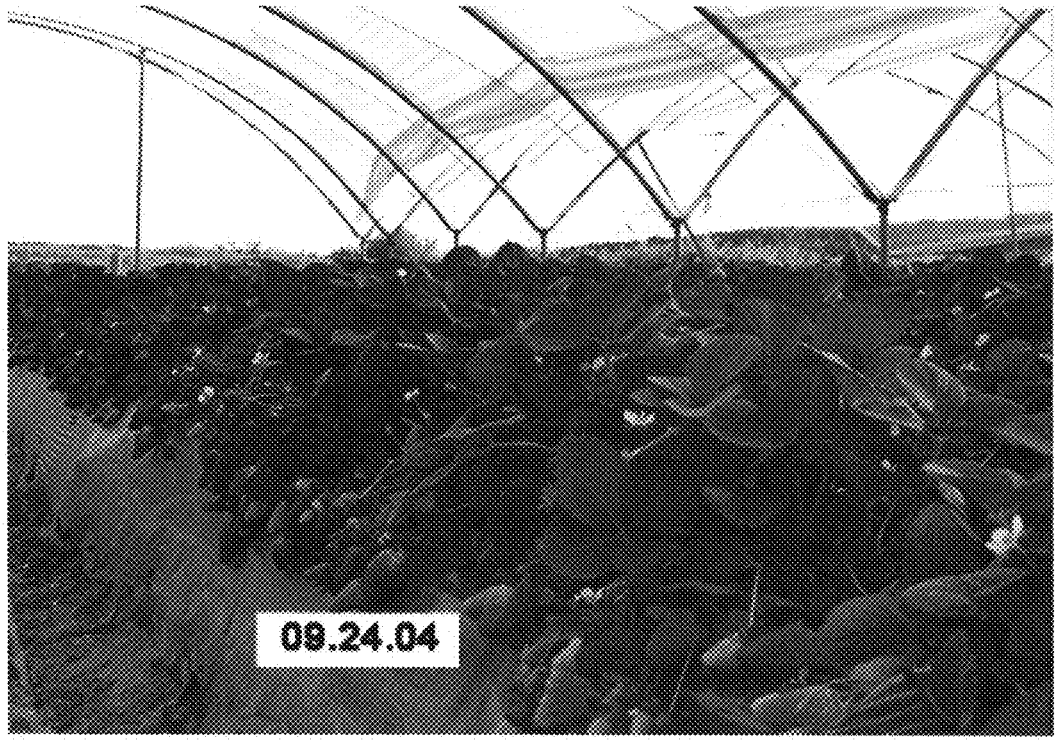
Figure 3:
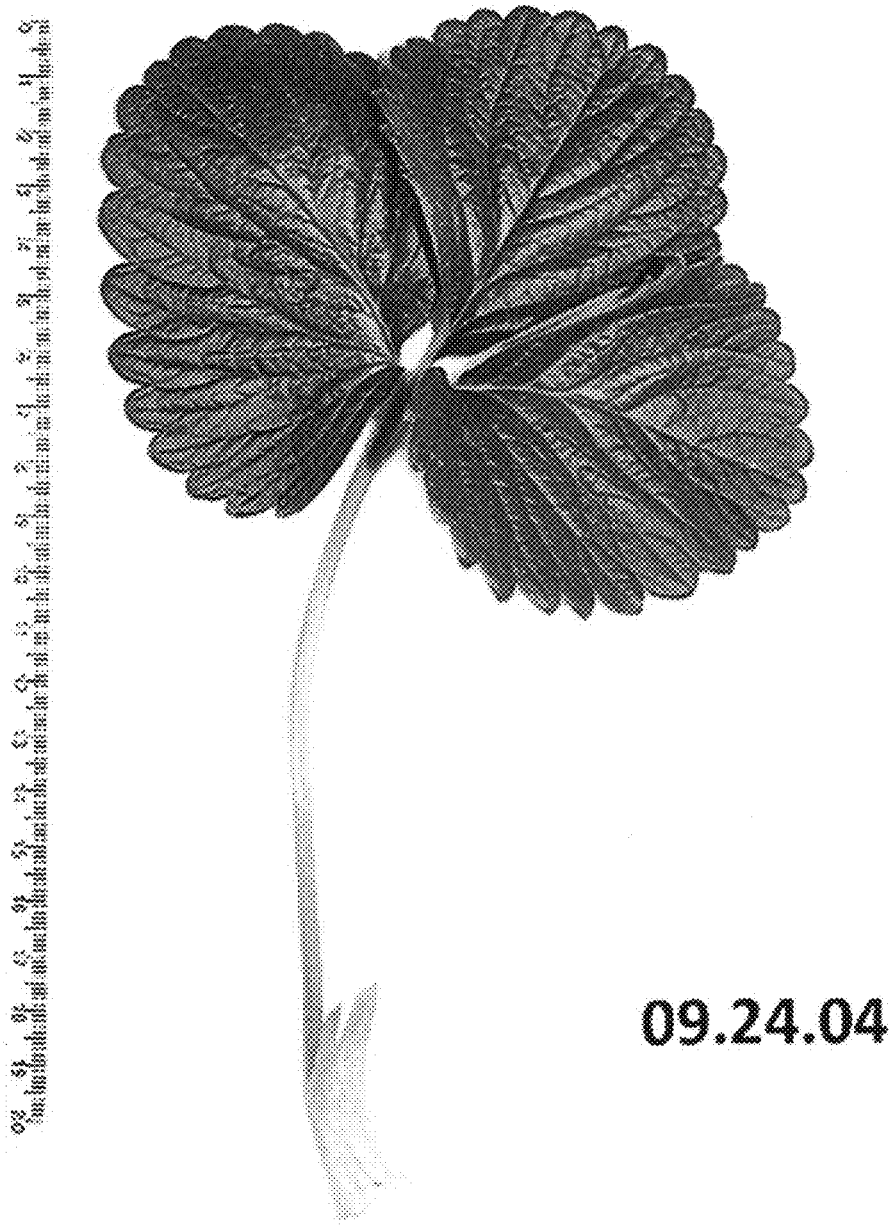
FIG. 3 shows the upperside of a complete leaf of the new variety (designated 09.24.04). In its we can see that the leaf color of upperside is RHS green group color (near 138 A to 139 B).
Figure 4:
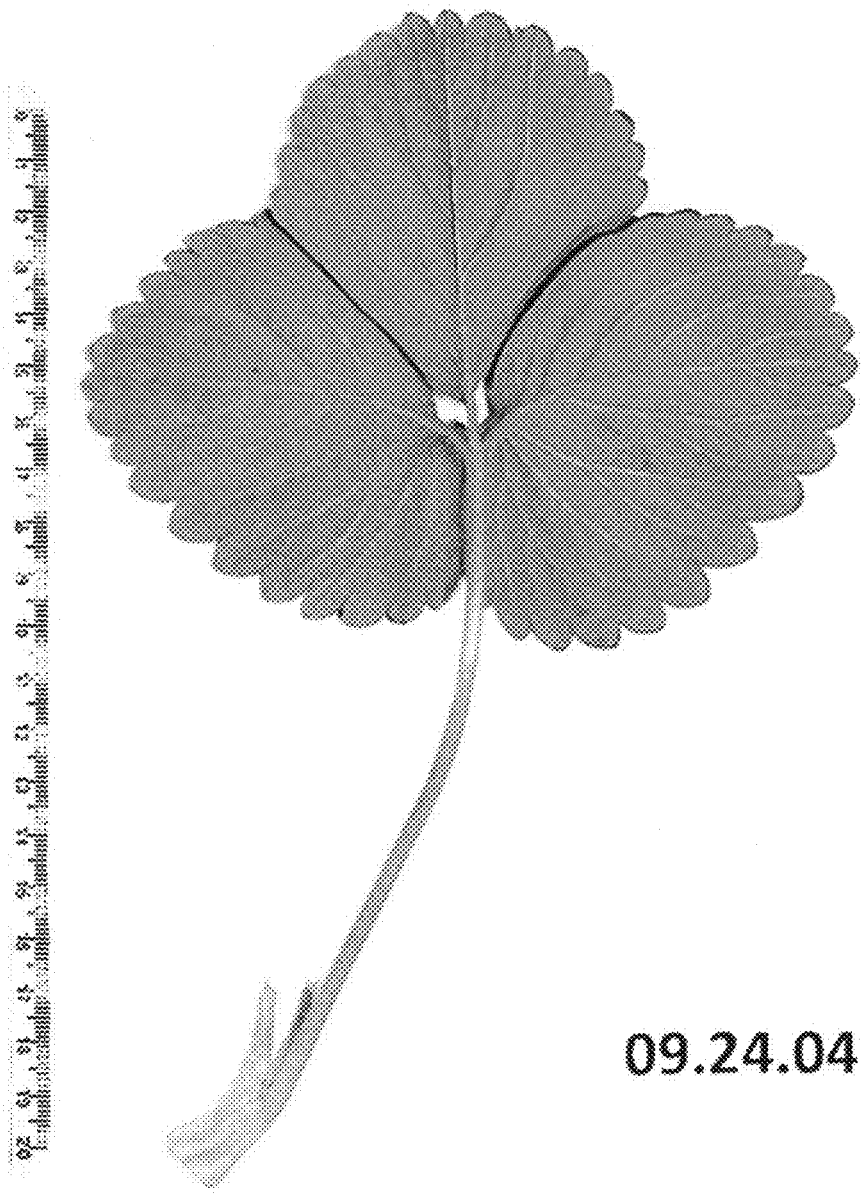
FIG. 4 shows the underside of a complete leaf of the new variety (designated 09.24.04). The leaf color of underside is RHS green group color (near 138 D to 138 C).
Figure 5:
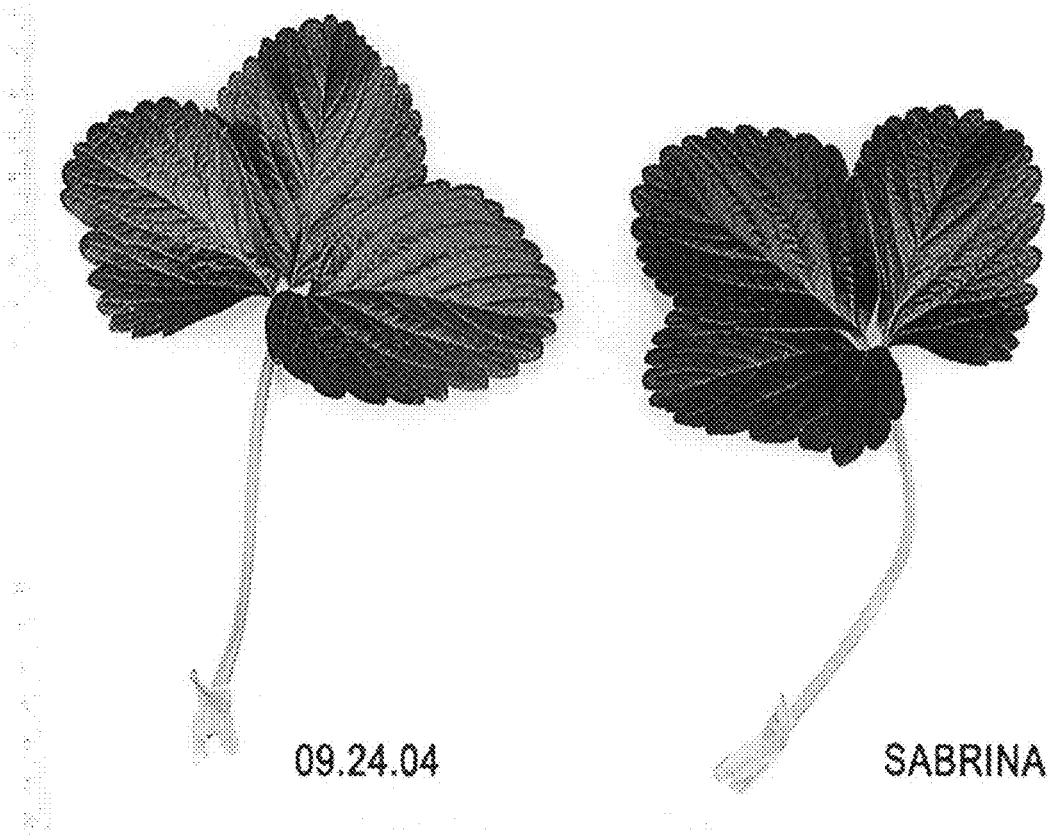

FIG. 5 shows the upperside of a complete leaf of the new variety (designated 09.24.04), with a RHS green group color (near 138 A to 139 B), in comparison with the upperside of a complete leaf of strawberry variety 'Sabrina' (U.S. Plant Pat. No. 22,506), with a RHS green group color (near 135 A to 136 A).

Figure 6:
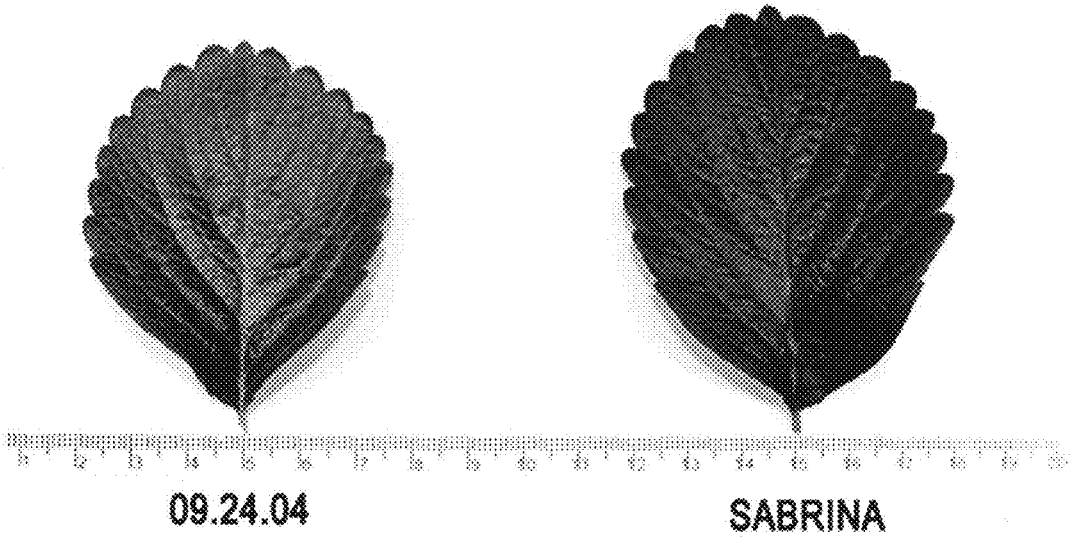

FIG. 6 shows the terminal leaflet of the new variety (designated 09.24.04) in comparison with the terminal leaflet of the strawberry variety 'Sabrina' (U.S. Plant Pat. No. 22,506). We can appreciate that the terminal leaflet in strawberry variety 'Sabrina' (U.S. Plant Pat. No. 22,506) is is much longer than broad, whereas in the new variety (designated 09.24.04) is moderately longer than broad.

Figure 7:
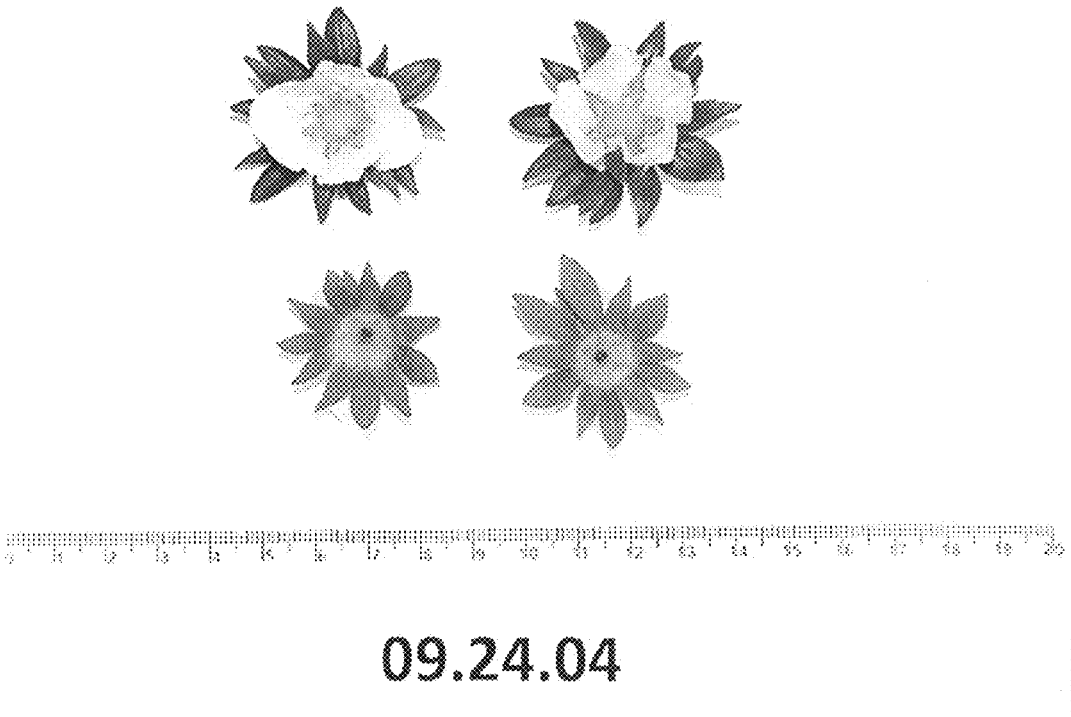

FIG. 7 shows several flowers of the new variety (designated 09.24.04).

Figure 8:
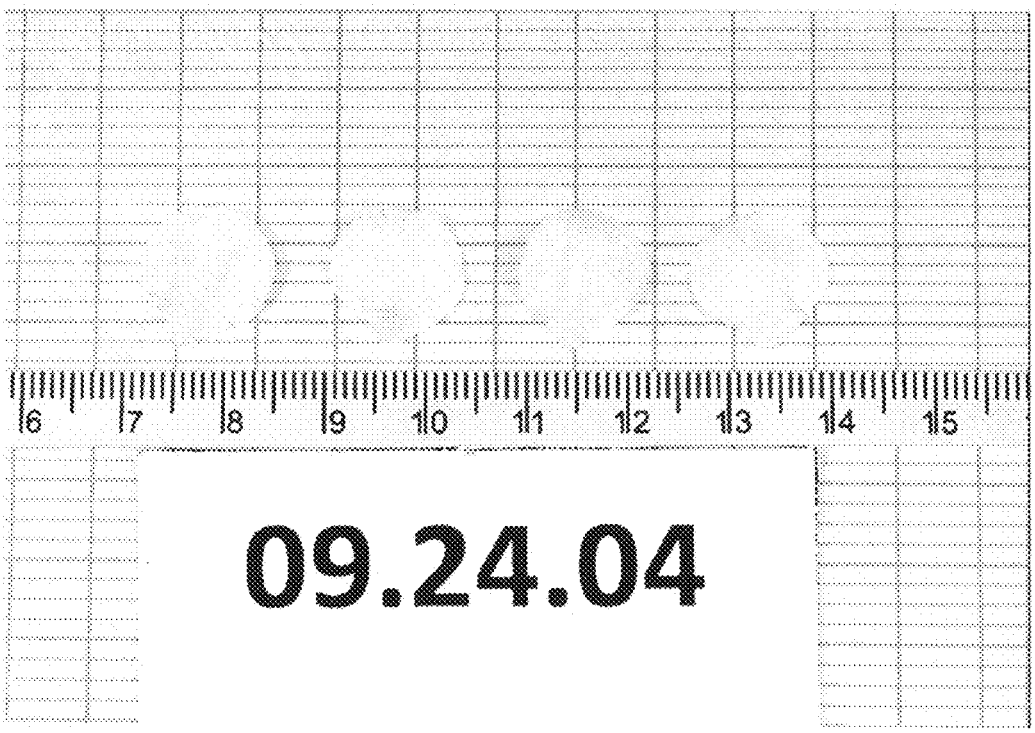

FIG. 8 shows several petals of the new variety (designated 09.24.04).

Figure 9:
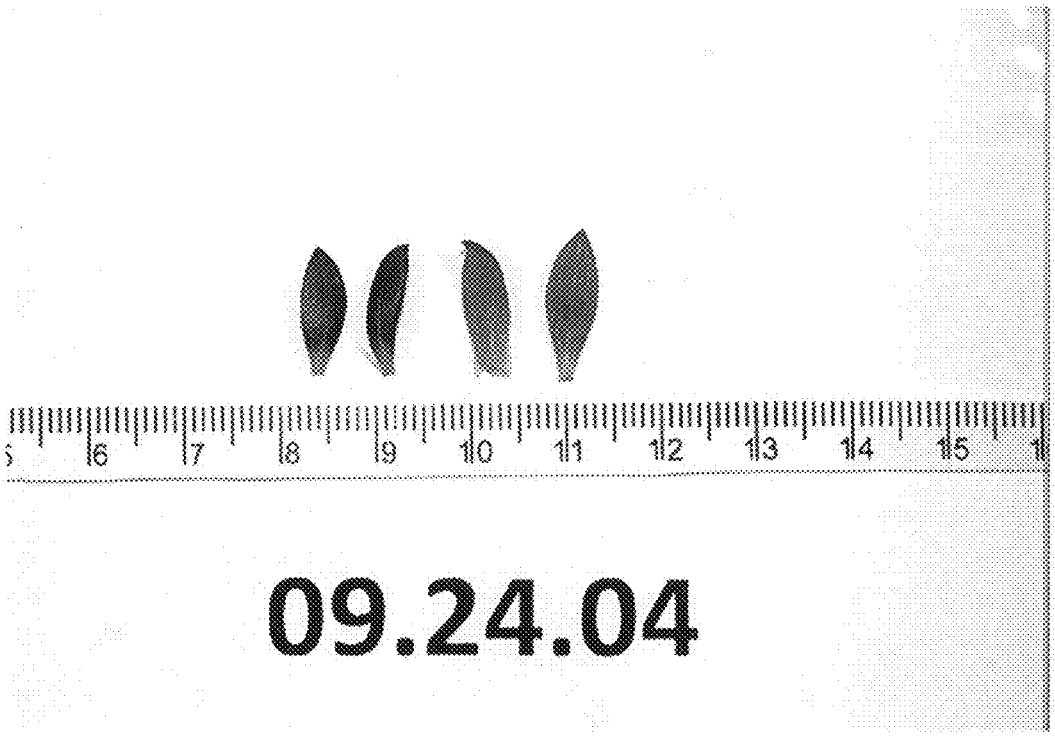

FIG. 9 shows upperside and underside of typical sepals of the new variety (designated 09.24.04).

Figure 10:
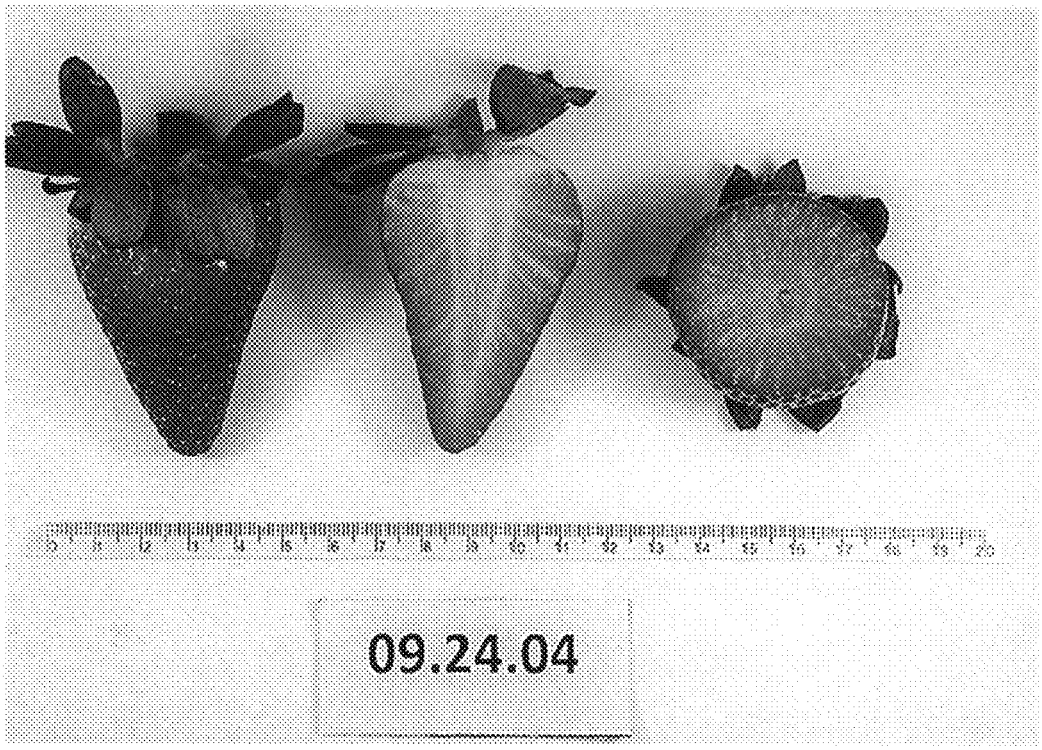

FIG. 10 shows typical fruit of the new variety (designated 09.24.04) whole, sliced and in cross section, illustrating the typical medium red fruit color (RHS red group near 41 A to 42 A), the typical orange red flesh coloration (RHS orange-red group near 33 B to 33 A) lightening toward the center, with an absent or weakly expressed hollow center.

Figure 11:
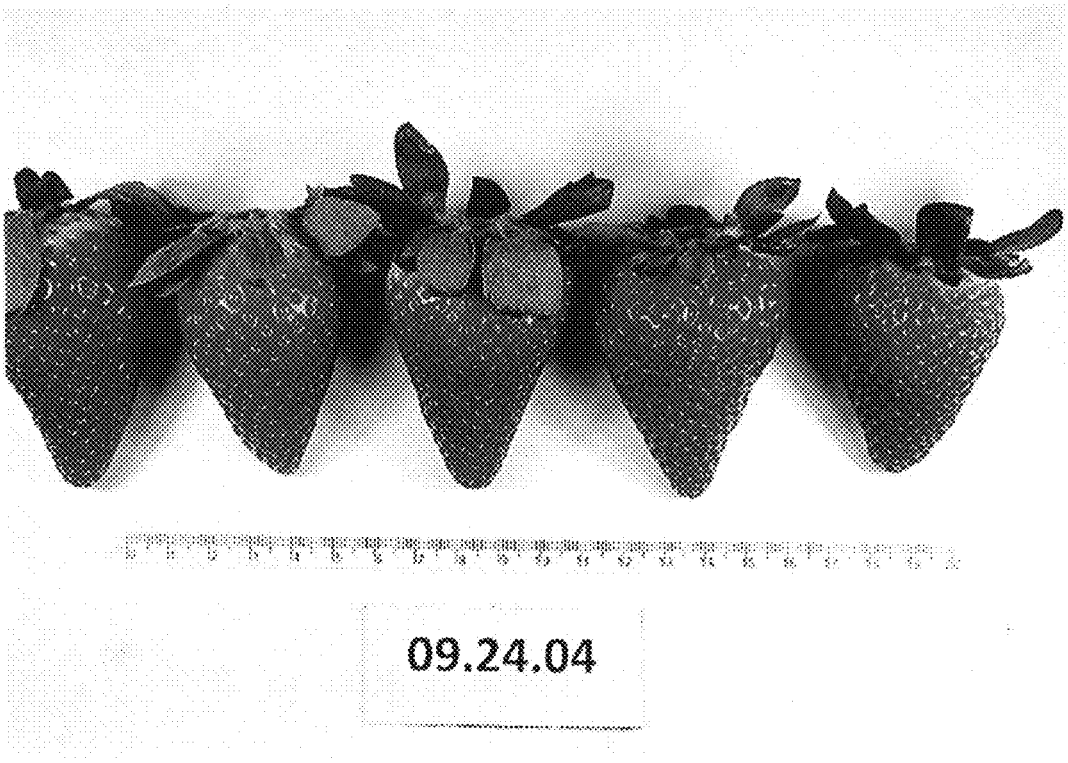

FIG. 11 shows several typical fruits of the new variety (designated 09.24.04) illustrating the typical conical shape and medium red fruit color (RHS red group near 41 A to 42 A).

Figure 12:
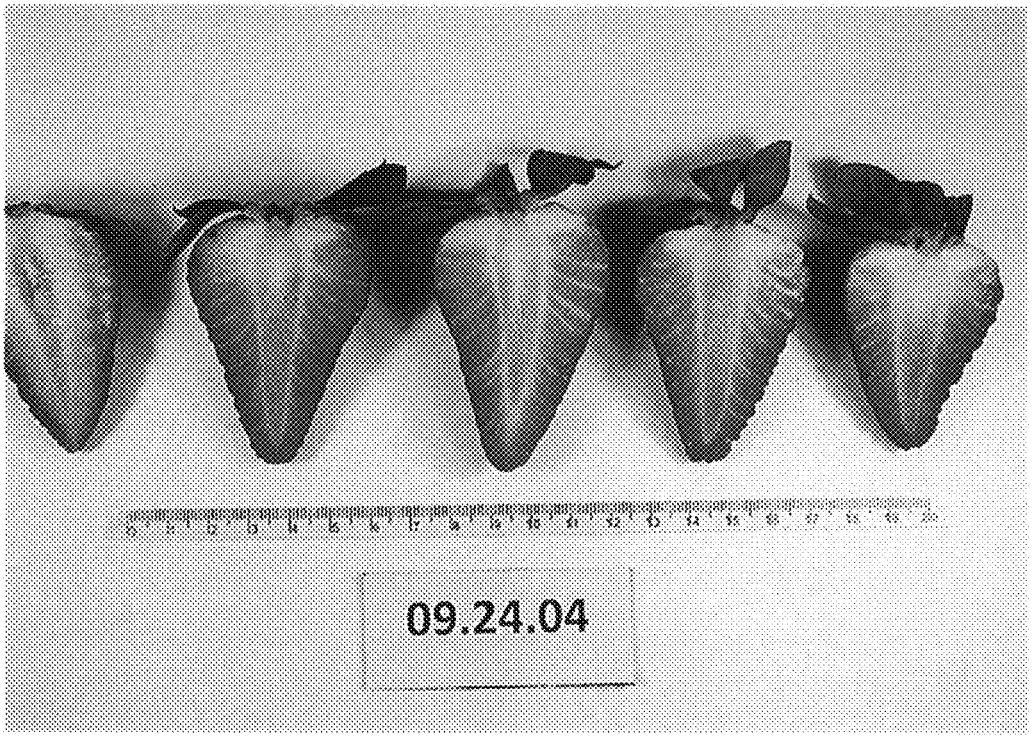

FIG. 12 shows several typical fruits of the new variety (designated 09.24.04) in cross section illustrating the typical orange red flesh coloration (RHS orange-red group near 33 B to 33 A) lightening toward the center, with an absent or weakly expressed hollow center.

Figure 13:
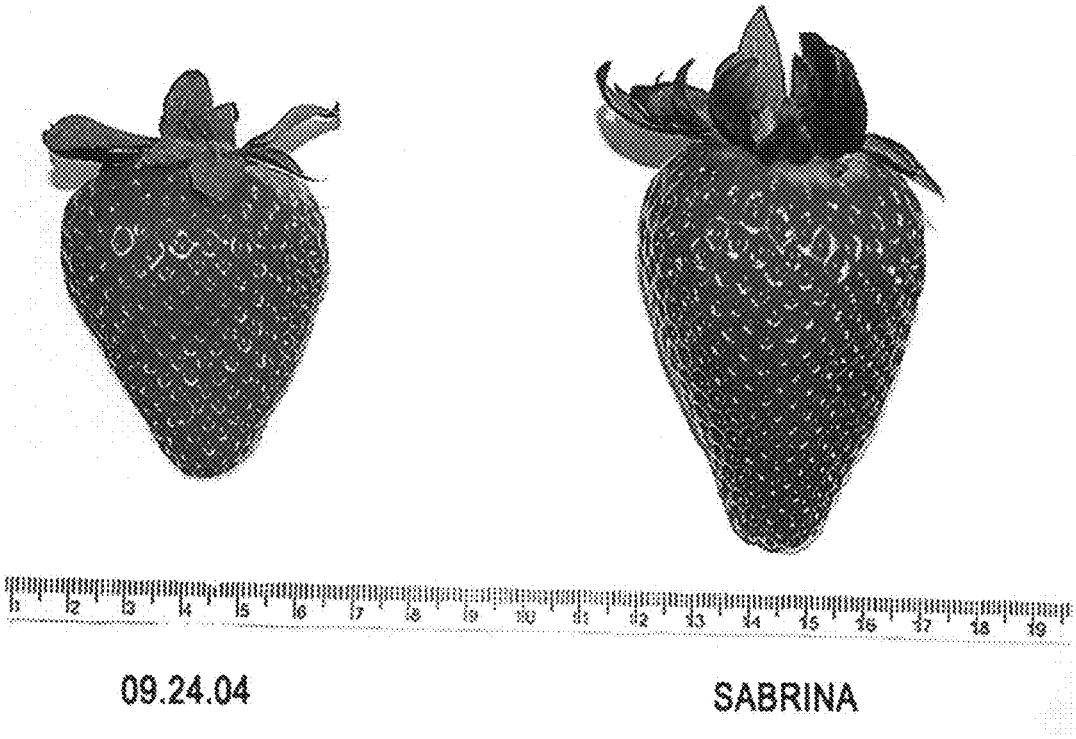

FIG. 13 shows the comparison between whole fruits of the new variety (designated 09.24.04) and the strawberry variety 'Sabrina' (U.S. Plant Pat. No. 22,506). In it we can see that the fruit size in 'Sabrina' (U.S. Plant Pat. No. 22,506) is larger than in the new variety (designated 09.24.04) and the fruits of the strawberry variety 'Sabrina' (U.S. Plant Pat. No. 22,506) show a red fruit color (RHS red group near 43 B to 43 A), whereas in the new variety (designated 09.24.04) the fruits show an medium red fruit color (RHS red group near 41 A to 42 A).

Figure 14:
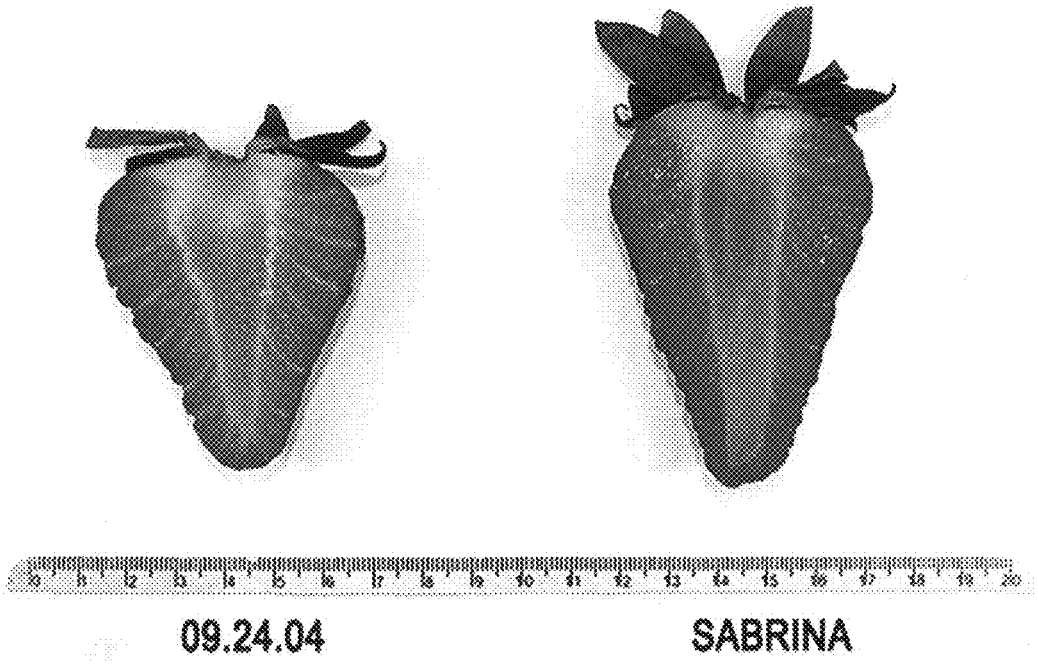

FIG. 14 shows the comparison between sliced fruits of the new variety (designated 09.24.04) and the strawberry variety 'Sabrina' (U.S. Plant Pat. No. 22,506). In it we can see that the fruit color of flesh in fruits of the strawberry variety 'Sabrina' (U.S. Plant Pat. No. 22,506) is red (RHS red group (near 41 B to 41 A), whereas the color of flesh in fruits of the new variety (designated 09.24.04) is orange red (RHS orange-red group near 33 B to 33 A).

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural Society, London, England, 1995.

The following detailed description of the new variety is based upon observations taken of plants and fruits grown under tunnel, in the farm La Mogalla, in Cartaya (Huelva), Spain, 7° W., 37° N., 45 feet elevation.

PROPAGATION

The new variety is principally propagated by way of runners. Although propagation by runners is presently preferred, other known methods of propagating strawberry plants may be used. Strawberries root well after transplanting.

The term "blistering" used herein refers to the texture or rugosity or surface undulation inherent to leaves and is generally a constant characteristic.

'Planasa 0949' is a short day variety that needs an induction to flowering by chilling, such as occurs at a high elevation nursery (fresh plant) or with cold storage (referred to as a frigo plant). Usually a short time is sufficient. 'Planasa 0949' is self-fertile. It produces large quantities of pollen throughout the seasons and pollination is generally good as there are very few malformed fruit.

Trials were performed in Cartaya (Huelva), Spain, about 7° W, 37° N, 45 feet elevation. Plants Were planted on October 13 with a sample size of two repetitions and 250 plants per repetition. After planting, plants are grown in raised beds cover with plastic and with small holes in plastic walls, under tunnels. Water and fertilizer are applied trough drip irrigation.

GENERAL

Table 1 shows the Accumulated production of Commercial Quality Fruit (g/plant) of the new variety 'Planasa 0949' when compared to its closest varieties 'Sabrina' and 'Florida Radiance' during the months of February, March, April and May.

TABLE 1

| Variety | 26-Fb | 30-Mr | 24-Ap | 11-My |
|---|---|---|---|---|
| Planasa 0949 | 61 | 274 | 696 | 830 |
| SABRINA | 47 | 237 | 809 | 950 |
| Florida Radiance | 99 | 313 | 708 | 892 |

Table 2 shows the Total Yield from October 13 and fruit weight average of the new variety 'Planasa 0949' when compared to its closest varieties 'Sabrina' and 'Florida Radiance' to May 11.

TABLE 2

| Variety | 1st + 2nd Quality Fruit | TOTAL (1st Quality + 2nd Quality) | Weight (g/fruit) |
|---|---|---|---|
| Planasa 0949 | 830 + 259 | 1089 | 27-25 |
| SABRINA | 950 + 279 | 1229 | 26-24 |
| Florida Radiance | 892 + 254 | 1146 | 25-23 |

Table 3 shows the Production Total, to May 11 of First Quality Fruit (1st quality) and Second Quality Fruit (2nd quality) in g/plant, of the new variety 'Planasa 0949' when compared to its closest varieties 'Sabrina' and 'Florida Radiance'.

TABLE 3

| Variety | 1st Quality | 2nd Quality | TOTAL (1st Quality + 2nd Quality) | % 2nd Quality |
|---|---|---|---|---|
| Planasa 0949 | 830 | 259 | 1089 | 24 |
| SABRINA | 950 | 279 | 1229 | 22 |
| Florida Radiance | 892 | 254 | 1146 | 22 |

% 2nd Quality = (2nd Quality/TOTAL) × 100

Table 4 shows the Weight (g/Fruit) at two dates: March 30 and May 11 of the new variety 'Planasa 0949' when compared to its closest varieties 'Sabrina' and 'Florida Radiance'.

TABLE 4

| Variety | 30 March WEIGHT | 11 May WEIGHT |
|---|---|---|
| Planasa 0949 | 27 | 25 |
| SABRINA | 26 | 24 |
| Florida Radiance | 25 | 23 |

WEIGHT is shown as the average weight per fruit (g/fruit) in First Quality Fruits.

Table 5 shows a comparison of the fruit analysis between the new variety 'Planasa 0949' and its closest varieties 'Sabrina' and 'Florida Radiance'.

TABLE 5

FRUIT ANALYSIS

| | Planasa 0949 (09.24.04) | Sabrina | Florida Radiance |
|---|---|---|---|
| Firmness (Kg) | 0.50 | 0.50 | 0.60 |
| Humidity & Volatile Matter (%) | 93.10 | 92.20 | 92.50 |
| Dry Matter (%) | 6.90 | 7.80 | 7.50 |
| pH (to 20°) | 3.70 | 3.70 | 3.70 |
| Acidity as Anhydride Citric (%) | 0.52 | 0.48 | 0.50 |
| Soluble Solids (° Brix) | 6.60 | 7.50 | 7.00 |
| Maturity Index | 12.69 | 15.62 | 14.00 |
| Content in Ascorbic Acid (ppm) | 25.30 | 21.10 | 31.60 |
| Dominant Tonality (nm) | 490 | 495 | 490 |
| Luminosity: Transmittance to 460 nm | 66.80 | 54.90 | 51.80 |
| Number of Units per kg | 25 | 31 | 24 |
| Median mass (g) | 44.4 | 34.6 | 46.6 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the weight of the residual left from the trituration of the fruit after the drying process at a temperature of 103° C.±2° C. until reaching constant weight.

(%) Dry Matter=(Weight Dry Matter/Weight Fresh Matter)×100

Humidity & Volatile Matter: Represents the content in volatile matters and water of the fruits.

(%) Humidity & Volatile Matter=100−% Dry Matter

Maturity Index: Relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety:

Variety: 'Planasa 0949'.

Breeder ref: 09.24.04.

Classification: *Fragaria* L.

Plant:

*Growth habit*.—Upright.

*Density of foliage*.—Medium.

*Vigor*.—Medium.

*Height*.—Medium, about 24 cm.

*Width*.—Medium, about 21 cm.

Leaf:

*Upper side color*.—RHS green group color (near 138 A to 139 B).

*Underside color*.—RH. yellow-green group color (near 138 D to 138 C).

*Length*.—About 8 cm.

*Width*.—About 14 cm.

*Shape in cross section*.—Concave.

*Leaf surface undulation or blistering*.—Absent or weak.
*Number of leaflets*.—Three only.
*Glossiness*.—Medium.
*Variegation*.—Absent.

Leaf stem characteristics:
*Color*.—RHS yellow-green group (near 145 B to 145 A).
*Position of hairs*.—Slightly outwards.
*Length*.—Medium, about 14 cm.

Terminal leaflet:
*Length/width ratio*.—Moderately longer.
*Length*.—Medium, about 6.0 cm to 6.5 cm.
*Width*.—Medium, about 5.0 cm to 5.5 cm.
*Shape of base*.—Acute.
*Margin*.—Crenate.
*Shape in cross section*.—Concave.

Petiole:
*Attitude of hairs*.—Slightly outwards.
*Color*.—RHS yellow-green group (near 145 B to 145 A).
*Length*.—Medium, about 14 cm.

Stipule:
*Anthocyanin coloration*.—Absent or very weak, RHS yellow-green group coloration (near 145 D to 145 C).
*Length*.—Medium, about 15 cm.

Stolons:
*Number*.—Medium, about 8.
*Thickness*.—Medium, about 3.0 mm to 3.5 mm.
*Pubescence density*.—Medium.
*Anthocyanin coloration*.—Absent or very weak, RHS yellow-green group coloration (near 145 D to 145 C).
*Color*.—RHS yellow-green group (near 145 B to 145 A).
*Length*.—Medium, about 34 cm to 38 cm.

Inflorescence:
*Number of flowers*.—Medium, about 6 to 8.
*Position relative to foliage*.—Level with.

Pedicel:
*Attitude/position of hairs*.—Slightly outwards.

Flower:
*Diameter/size*.—Medium.
*Size of calyx relative to corolla*.—Larger.
*Arrangement of petals*.—Overlapping.
*Diameter primary flowers*.—Long, about 2.9 cm to 3.4 cm.
*Diameter secondary flowers*.—Medium, about 2.7 cm to 3.1 cm.
*Number of petals*.—About 5 to 7.
*Fragrance*.—No significant fragrance.
*Time from bloom to mature fruit* (*in Huelva, Spain*).—About 30 days to 35 days.
*Stamens*.—Present and numerous with pollen present, fertile and abundant.
*Stamens length*.—Approximately 3.6 mm to 3.7 mm.
*Stamens color*.—RHS white group (near 155 D to 155 C).
*Anthers*.—Generally average in size.
*Anthers color*.—RHS yellow group (near 12 C to 12 B) and darkening with advanced maturity.
*Pollen*.—Fertile and abundant.
*Pollen color*.—RHS yellow orange group (near 16 C to 16 B).
*Pistils*.—Abundant.
*Pistils size*.—Medium.
*Pistils color*.—RHS yellow group (near 13 D to 13 C).

Petal:
*Length/width ratio*.—Equal.
*Length*.—Long, about 12 mm to 14 mm.
*Width*.—Long, about 11 mm to 13 mm.
*Shape*.—Rounded.
*Color of upper side*.—RHS white group (near 155 D to 155 C).

Fruiting truss:
*Attitude*.—Semi-erect.

Fruit:
*Ratio of length/maximum width*.—Moderately longer.
*Color*.—RHS red group (near 41 A to 42 A).
*Peduncle length of inflorescence stem of primary fruit*.—About 18 cm to 21 cm.
*Peduncle length of inflorescence stem of secondary fruit*.—About 13 cm to 15 cm.
*Peduncle of inflorescence stem color*.—RHS yellow-green group (near 145 C to 145 B).

Primary fruit:
*Length*.—Long, about 6.0 cm to 6.5 cm.
*Width*.—Medium, about 4.0 cm to 4.5 cm.

Secondary fruit:
*Length*.—About Long, about 5.0 cm to 5.5 cm.
*Width*.—Medium, about 3.5 cm to 4.0 cm.
*Size*.—Medium.
*Shape*.—Conical.
*Difference in shapes between primary and secondary fruits*.—Slight.
*Band without achenes*.—Absent or very narrow.
*Color of achenes*.—RHS orange to orange red group (near 29 A to 30 D).
*Evenness of surface*.—Even or very slightly uneven.
*Evenness of color*.—Even or very slightly uneven.
*Glossiness*.—Medium.
*Position of achenes*.—Below surface.
*Insertion of calyx*.—Level with fruit.
*Attitude of sepals*.—Outwards.
*Size/diameter of calyx in relation to diameter of fruit*.—Slightly larger. The calyx presents 6 to 7 sepals with lanceolate shape and 4 to 5 sepals in addition smaller than above mencionated with pointed shape.
*Color upper side of sepals*.—Green group (near 139 B to 139 A).
*Color underside of sepals*.—Yellow-Green group (near 144 B to 144 A).
*Length of sepals*.—Long, about 15 mm to 20 mm.
*Width of sepals*.—Long, about 7 mm to 9 mm.
*Adherence of calyx*.—Strong.
*Firmness*.—Firm.
*Color of flesh*.—RHS orange red (RHS orange-red group near 33 B to 33 A), lightening toward center.
*Distribution of orange red color of flesh*.—Only marginal.
*Hollow center*.—Absent or small.
*Color of core*.—RHS orange red group (near 32 D to 32 C).
*Sweetness*.—Medium. 6.60° Brix.
*Acidity*.—Medium. 0.52%.
*Time of flowering* (50% *of plants at first flower*).—Early.
*Time of ripening* (50% *of plants with ripe fruits*).—Early.

*Type of bearing*.—Not remontant.

*Chilling*.—Weak.

Disease resistance: No particular sensitivity to any disease or parasite has been observed for 'Planasa 0949'.

Storage qualities: 'Planasa 0949' fruit maintain their quality characteristics when keeping them in a frigo chamber at temperatures of about 2° C. during 48 hours. The fruit's color remains substantially the same.

Planting date: October 13 in the farm of La Mogalla, in Cartaya (Huelva), Spain, about 7° W, 37° N, 45 feet elevation.

10% Flowering (based on October 13 planting date): About November 11.

First mature fruits (based on October 13 planting date): About December 23.

Maturity (15-20 gms/plant) (based on October 13 planting date): About January 16.

Time of flowering data:

Time of flowers (50% of plants at first flower) (based on October 13 planting date): About December 7.

Time of ripening (based on October 13 planting date): After planting as aforesaid, plants are grown in raised beds cover with plastic and with small holes in plastic walls, under tunnel. Water and fertilizer were applied through drip irrigation. Time of ripening (50% of plants with ripe fruit) is about January 7.

I claim:

1. A new and distinct strawberry plant of the variety substantially as shown and described.

* * * * *